US00PP35475P2

(12) United States Plant Patent
Masor

(10) Patent No.: US PP35,475 P2
(45) Date of Patent: Nov. 14, 2023

(54) ***VERBENA* PLANT NAMED 'BALFIREMINT'**

(50) Latin Name: ***Verbena* hybrid**
Varietal Denomination: Balfiremint

(71) Applicant: Ball Horticultural Company, West Chicago, IL (US)

(72) Inventor: Laura L. Masor, Buda, TX (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 18/132,674

(22) Filed: Apr. 10, 2023

(51) Int. Cl.
*A01H 5/02* (2018.01)
*A01H 6/86* (2018.01)

(52) U.S. Cl.
USPC ..... Plt./308

(58) Field of Classification Search
USPC ..... Plt./308
See application file for complete search history.

(56) References Cited

PUBLICATIONS https://www.gardentags.com/plant-encyclopedia/verbena-sweet-stripe/34704 (Retrieved from the Internet on Aug. 1, 2023).*

* cited by examiner

*Primary Examiner* — Susan McCormick Ewoldt
(74) *Attorney, Agent, or Firm* — Audrey Charles

(57) ABSTRACT

A new and distinct cultivar of *Verbena* plant named 'Balfiremint', characterized by its medium red and light pink bicolored flowers, dark green-colored foliage, and moderately vigorous, mounded-spreading growth habit, is disclosed.

1 Drawing Sheet

Latin name of genus and species of plant claimed: *Verbena* hybrid.

Variety denomination: 'Balfiremint'.

BACKGROUND OF THE INVENTION

The present invention relates to a new and distinct cultivar of *Verbena* plant botanically known as *Verbena* hybrid and hereinafter referred to by the cultivar name 'Balfiremint'.

The new cultivar originated in a controlled breeding program in Arroyo Grande, California. The objective of the breeding program was the development of *Verbena* cultivars that are suited for use in hanging baskets, durable to environmental stresses, and have a mounded-spreading growth habit.

The new *Verbena* hybrid cultivar is a natural sport of the proprietary *Verbena* hybrid breeding selection coded VRB-11702-04, not patented, characterized by its dark red-colored flowers, dark green-colored foliage, and moderately vigorous, mounded-spreading growth habit. The new cultivar was discovered as a side shoot and selected during June 2019 in a controlled environment in Arroyo Grande, California.

Asexual reproduction of the new cultivar by terminal stem cuttings since June 2019 in Arroyo Grande, California and West Chicago, Illinois has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balfiremint' as a new and distinct cultivar of *Verbena* plant:

1. Medium red and light pink bicolored flowers;
2. Dark green-colored foliage; and
3. Moderately vigorous, mounded-spreading growth habit.

Plants of the new cultivar differ from plants of the female parent primarily in having medium red and light pink bicolored flowers unlike the solid red-colored flowers of the female parent.

Of the many commercially available *Verbena* cultivars, the most similar in comparison to the new cultivar is Firehouse Light Pink 'Balfirelitpi', not patented. However, in side by side comparisons, plants of the new cultivar differ from plants of 'Balfirelitpi' in at least the following characteristics:

1. Plants of the new cultivar are less vigorous than plants of 'Balfirelitpi'; and
2. Plants of the new cultivar have medium red and light pink bicolored flowers unlike the light pink-colored flowers of plants of 'Balfirelitpi'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balfiremint'. The plants were approximately 16-weeks old. The plants were grown in 4.5-inch containers for approximately 11 weeks in a greenhouse in West Chicago, Illinois. Plants were given one pinch at transplant.

DETAILED BOTANICAL DESCRIPTION

Figure 1:
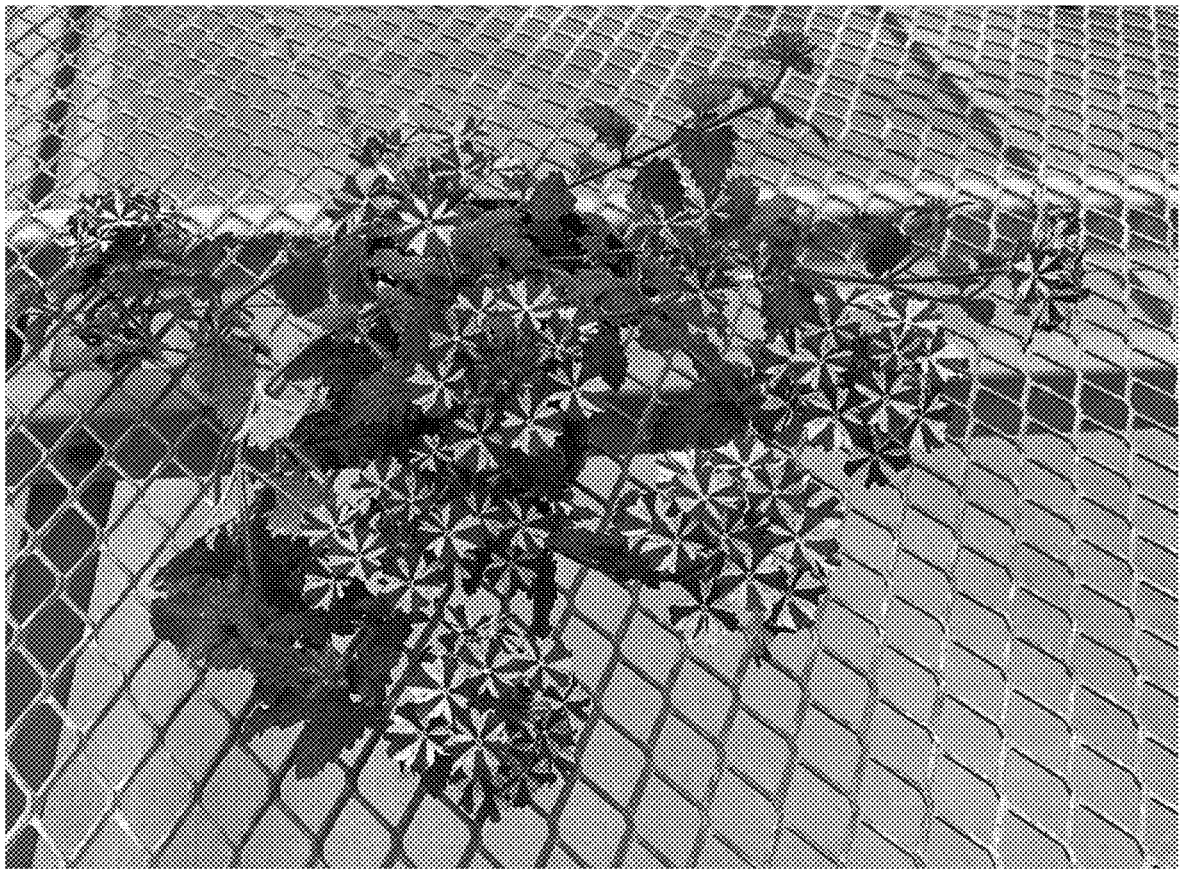
FIG. 1 illustrates a side view of the overall growth and flowering habit of 'Balfiremint'.
Figure 2:
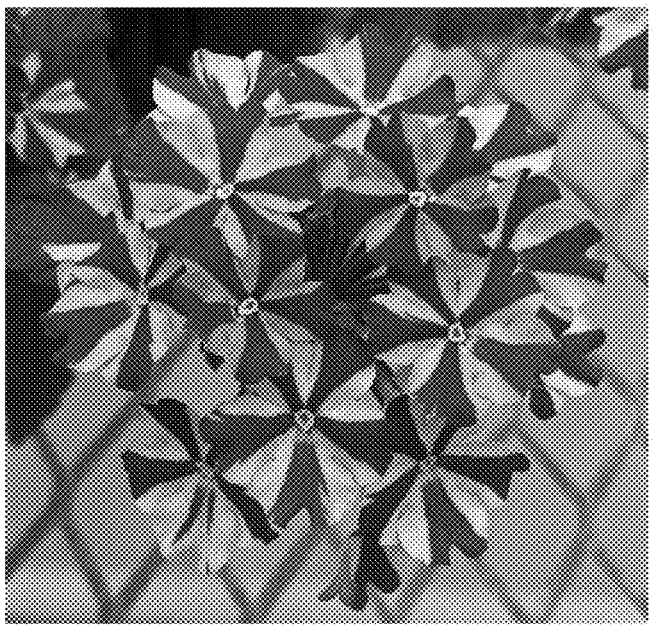
FIG. 2 illustrates a close-up view of an individual inflorescence of 'Balfiremint'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in February 2023 under natural light conditions in Naperville, Illinois.

The following descriptions and measurements describe approximately 16-week-old plants produced from cuttings from stock plants and grown in a polycarbonate greenhouse under conditions comparable to those used in commercial practice. The plants were grown in West Chicago, Illinois in 4.5-inch containers for approximately 11 weeks utilizing a soilless growth medium. Plants were given one pinch at transplant. Greenhouse temperatures were maintained at approximately 68° F. to 70° F. (20° C. to 21° C.) during the day and approximately 60° F. to 65° F. (16° C. to 18° C.) during the night. Supplemental lighting was used. Measurements and numerical values represent averages of typical plants.

Botanical classification: *Verbena* hybrid 'Balfiremint'.

Parentage:

*Parent*.—Proprietary *Verbena* hybrid breeding selection coded VRB-11702-04, not patented.

Propagation:

*Type cutting*.—Terminal stem.

*Time to initiate roots*.—Approximately 6 to 9 days.

*Time to produce a rooted cutting*.—Approximately 24 to 28 days.

*Root description*.—Fibrous.

*Rooting habit*.—Freely branching.

Plant description:

*Commercial crop time*.—Approximately 5 to 7 weeks from a rooted cutting to finish in a 10 cm container.

*Growth habit and general appearance*.—Moderately vigorous, mounded-spreading.

*Size*.—Height from soil level to top of plant plane: Approximately 13.0 cm. Width: Approximately 42.0 cm.

*Branching habit*.—Freely branching, pinching enhances basal branching. Quantity of main branches per plant: Approximately 6.

*Branch*.—Shape: Square in cross section. Strength: Strong. Length: Approximately 18.5 cm. Diameter: Approximately 3.0 mm. Length of central internode: Approximately 3.5 cm. Texture: Densely pubescent with a mixture of glandular and nonglandular hairs. Gland color: Colorless, transparent. Color of young stems: 144A. Color of mature stems: 146B.

Foliage description:

*General description*.—Quantity of leaves per main branch: Approximately 10. Fragrance: None detected. Form: Simple. Arrangement: Opposite.

*Leaves*.—Aspect: Perpendicular to stem, obtuse angle with age. Shape: Ovate to oblong. Margin: Crenate. Apex: Broadly acute. Base: Truncate. Venation pattern: Pinnate. Length of mature leaf: Approximately 4.2 cm. Width of mature leaf: Approximately 3.0 cm. Texture of upper surface: Densely pubescent. Texture of lower surface: Densely pubescent with a mixture of glandular and nonglandular hairs. Gland color: Colorless, transparent. Color of upper surface of young and mature foliage: Closest to but darker than 137A with venation of 147C. Color of lower surface of young and mature foliage: Closest to but darker than 138A with venation of 147C.

*Petiole*.—Length: Approximately 1.0 cm. Diameter: Approximately 2.0 mm. Texture: Densely pubescent with a mixture of glandular and nonglandular hairs. Gland color: Colorless, transparent. Color: 147C.

Flowering description:

*Flowering habit*.—'Balfiremint' is freely flowering under outdoor growing conditions with substantially continuous blooming from spring through autumn and year-round in greenhouse environment.

*Lastingness of individual flower on the plant*.—Approximately 5 to 7 days.

Inflorescence description:

*General description*.—Type: Corymb. Shape: Hemispherical. Quantity per plant: Approximately 9. Fragrance: None detected. Length or height: 3.0 cm. Width: Approximately 6.5 cm. Quantity of fully open flowers per inflorescence: Approximately 16.

*Peduncle*.—Strength: Strong. Aspect: Erect. Length: Approximately 3.0 cm. Diameter: Approximately 2.0 mm. Texture: Densely pubescent with a mixture of glandular and nonglandular hairs. Gland color: Colorless, transparent. Color: 144A.

Flower description:

*General description*.—Type: Sessile, salverform.

*Bud*.—Rate of opening: Generally takes 2 to 3 days for bud to progress from first color to fully open flower. Quantity of unopened inflorescences per plant: Approximately 8.

*Bud just before opening*.—Shape: Elongated, globular at apex. Length: Approximately 1.6 cm. Diameter: Approximately 3.0 mm. Color: Petal portion 37B, sepal portion 137B.

*Corolla*.—Shape: Round. Diameter: Approximately 2.2 cm. Depth: Approximately 3.0 cm.

*Petals*.—Quantity: 5, fused at base forming a tube. Shape: Obovate. Appearance: Matte. Margin: Entire. Apex: Emarginate. Length of upper petals from tube: Approximately 1.0 cm. Width of upper petals: Approximately 8.0 mm. Length of lateral petals from tube: Approximately 1.1 cm. Width of lateral petals: Approximately 9.0 mm. Length of lower petal from tube: Approximately 1.1 cm. Width of lower petal: Approximately 1.1 cm. Texture of upper surface: Glabrous with glandular pubescent base. Texture of lower surface: Sparsely pubescent with a mixture of glandular and nonglandular hairs. Gland color: Colorless, transparent. Color of upper surface when first open: Broad flared center of N45A bordered with 35D. Color of lower surface when first open: 37D with underlay of N45D in broad flared center. Color of upper surface when fully open: Broad flared center of N45B bordered with 37D. Color of lower surface when fully open: 38D with underlay of N45D in broad flared center. Color of whiskers surrounding the opening of the corolla tube: NN155D.

*Corolla tube*.—Length: Approximately 2.1 cm. Diameter at proximal end: Approximately 1.0 mm. Diameter at distal end: Approximately 2.0 mm. Texture of outer surface: Approximately upper half moderately glandular pubescent with lower portion glabrous. Gland color: Colorless, transparent. Texture of inner surface: Approximately upper half densely pubescent with lower portion glabrous. Color of outer surface: 145D with 155C at base. Color of inner surface: NN155D with 145C at throat opening.

*Calyx*.—Shape: Tubular with 5 acute tips. Length: Approximately 1.4 cm. Width: Approximately 3.0 mm.

*Sepals*.—Quantity per flower: 5, fused at base. Shape: Linear. Apex: Acute. Length: Approximately 1.4 cm. Width: Approximately 1.0 mm. Texture of inner surface: Moderately pubescent. Texture of outer surface: Densely pubescent with a mixture of glandular and nonglandular hairs. Gland color: Colorless, transparent. Color of inner and outer surfaces: 137B.

*Stipules*.—Shape: Oblanceolate. Apex: Three acute tips arranged in a cross shape. Length: Approximately 7.0 mm. Width at base: Approximately 3.0 mm. Texture of inner surface: Glabrous. Texture of outer surface: Densely pubescent with a mixture of glandular and nonglandular hairs. Gland color: Colorless, transparent. Color of inner and outer surfaces: 137A with 144A at base.

*Reproductive organs*.—Androecium: Stamen quantity: 4, didynamous. Stamen length of longer pair: Approximately 2.0 mm. Stamen length of shorter pair: Approximately 1.0 mm. Anther shape: Bilobed, ovoid. Anther length: Approximately 1.0 mm. Anther color: N144D. Pollen amount: Sparse. Pollen color: 1D. Gynoecium: Pistil quantity: 1 per flower. Pistil length: Approximately 1.7 cm. Stigma shape: Bifid. Stigma length: Approximately 1.0 mm. Stigma color: 137A and 187A. Style length: Approximately 1.6 cm. Style color: 145D with 145B near stigma. Ovary diameter: Approximately 1.0 mm. Ovary texture: Glabrous. Ovary color: 144A.

Seed and fruit production: Neither seed nor fruit production has been observed.

Disease and pest resistance: Resistance to pathogens and pests common to *Verbena* has not been observed.

What is claimed is:

1. A new and distinct cultivar of *Verbena* plant named 'Balfiremint', substantially as herein illustrated and described.

* * * * *